(12) United States Patent
O'Neil et al.

(10) Patent No.: US 9,162,041 B2
(45) Date of Patent: Oct. 20, 2015

(54) NUCLEUS AUGMENTATION DELIVERY DEVICE AND TECHNIQUE

(71) Applicant: DePuy Synthes Products, LLC, Raynham, MA (US)

(72) Inventors: Michael J O'Neil, West Barnstable, MA (US); Christine Rusbarsky, Norton, MA (US); John Riley Hawkins, Cumberland, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 13/740,503

(22) Filed: Jan. 14, 2013

(65) Prior Publication Data

US 2013/0131634 A1 May 23, 2013

Related U.S. Application Data

(63) Continuation of application No. 13/438,455, filed on Apr. 3, 2012, now Pat. No. 8,357,199, and a continuation of application No. 11/260,768, filed on Oct. 27, 2005, now Pat. No. 8,197,545.

(51) Int. Cl.
*A61F 2/44* (2006.01)
*A61M 25/10* (2013.01)
(Continued)

(52) U.S. Cl.
CPC .............. *A61M 25/10* (2013.01); *A61F 2/4611* (2013.01); *A61F 2/4657* (2013.01); *A61B 17/8808* (2013.01); *A61B 17/8816* (2013.01);
(Continued)

(58) Field of Classification Search
CPC .................. A61F 2/442; A61F 2/4611; A61F 2002/30581; A61F 2/441; A61F 2/46
USPC ............................................ 623/17.11–17.16
See application file for complete search history.

(56) References Cited

U.S. PATENT DOCUMENTS 3,875,595 A * 4/1975 Froning ..................... 623/17.12
4,471,888 A 9/1984 Herb
(Continued)

FOREIGN PATENT DOCUMENTS

EP    460698    7/1992
EP    459464    4/1996
(Continued)

OTHER PUBLICATIONS

Meakin, J. et al., "Replacing the Nucleus Pulpasus of the Invertebral Disc", Clinical Biomechanics, 2001, vol. 16, pp. 560-565.
(Continued)

*Primary Examiner* — Mary Hoffman
*Assistant Examiner* — Tara R Carter
(74) *Attorney, Agent, or Firm* — Raymond N. Scott, Jr.

(57) ABSTRACT

A method of performing a procedure on an intervertebral disc includes inserting a cannulated delivery tube through an opening in an annulus fibrosus of the intervertebral disc, positioning an expandable portion of the tube within the opening in the annulus fibrosus, expanding the expandable portion into contact with the annulus fibrosus about the opening to create a seal between the expandable portion and the annulus fibrosus, performing a procedure through the cannulated delivery tube within the annulus fibrosis, removing the tube, and closing the opening in the annulus fibrosus.

19 Claims, 3 Drawing Sheets

(51) Int. Cl.
*A61F 2/46* (2006.01)
*A61B 17/88* (2006.01)

(52) U.S. Cl.
CPC ... *A61F2002/444* (2013.01); *A61F 2002/4435* (2013.01); *A61F 2002/4627* (2013.01); *A61F 2002/4663* (2013.01)

(56) References Cited

U.S. PATENT DOCUMENTS

| | | |
|---|---|---|
| 4,493,436 A | 1/1985 | Brokaw |
| 4,538,920 A | 9/1985 | Drake |
| 4,566,610 A | 1/1986 | Herb |
| 4,747,517 A | 5/1988 | Hart |
| 4,753,536 A | 6/1988 | Spehar |
| 4,767,026 A | 8/1988 | Keller |
| 4,771,919 A | 9/1988 | Ernst |
| 4,811,549 A | 3/1989 | Usami |
| 4,869,400 A | 9/1989 | Jacobs |
| 4,871,088 A | 10/1989 | Cox |
| 4,907,727 A | 3/1990 | Ernst |
| 4,974,756 A | 12/1990 | Pearson |
| 4,978,336 A | 12/1990 | Capozzi |
| 4,979,942 A | 12/1990 | Wolf |
| 4,981,241 A | 1/1991 | Keller |
| 4,989,758 A | 2/1991 | Keller |
| 4,995,540 A | 2/1991 | Colin |
| 5,002,576 A | 3/1991 | Fuhrmann |
| 5,005,735 A | 4/1991 | Keller |
| 5,020,694 A | 6/1991 | Pettengill |
| 5,033,650 A | 7/1991 | Colin |
| 5,078,587 A | 1/1992 | Bison |
| 5,080,262 A | 1/1992 | Herold |
| 5,082,147 A | 1/1992 | Jacobs |
| 5,092,845 A | 3/1992 | Chang |
| 5,126,090 A | 6/1992 | Egolf |
| 5,137,181 A | 8/1992 | Keller |
| 5,139,174 A | 8/1992 | Golias |
| 5,171,280 A | 12/1992 | Baumgartner |
| 5,224,628 A | 7/1993 | Keller |
| 5,248,068 A | 9/1993 | Goergen |
| 5,249,709 A | 10/1993 | Duckworth |
| 5,263,614 A | 11/1993 | Jacobsen |
| RE34,487 E | 12/1993 | Keller |
| 5,295,613 A | 3/1994 | Barthomeuf |
| 5,310,091 A | 5/1994 | Dunning |
| 5,333,760 A | 8/1994 | Simmen |
| 5,336,014 A | 8/1994 | Keller |
| 5,447,226 A | 9/1995 | Laine |
| 5,477,987 A | 12/1995 | Keller |
| 5,535,922 A | 7/1996 | Maziarz |
| 5,645,597 A | 7/1997 | Krapiva |
| 5,667,102 A | 9/1997 | Keller |
| 5,676,280 A | 10/1997 | Robinson |
| 5,722,829 A | 3/1998 | Wilcox |
| 5,788,122 A | 8/1998 | Keller |
| 5,800,549 A | 9/1998 | Bao |
| 5,819,988 A | 10/1998 | Sawhney |
| 5,875,928 A | 3/1999 | Muller |
| 5,887,755 A | 3/1999 | Hood, III |
| 5,888,220 A | 3/1999 | Felt |
| RE36,235 E | 6/1999 | Keller |
| 5,918,772 A | 7/1999 | Keller |
| 5,924,600 A | 7/1999 | Keller |
| 5,944,226 A | 8/1999 | Schiltz |
| 5,992,694 A | 11/1999 | Keller |
| 6,039,216 A | 3/2000 | Cummings |
| 6,047,861 A | 4/2000 | Vidal |
| 6,065,645 A | 5/2000 | Sawhney |
| 6,079,868 A | 6/2000 | Rydell |
| 6,089,407 A | 7/2000 | Gardos |
| 6,161,730 A | 12/2000 | Heusser |
| 6,165,218 A | 12/2000 | Husson |
| 6,176,396 B1 | 1/2001 | Hamada |
| 6,182,867 B1 | 2/2001 | Keller |
| 6,183,518 B1 | 2/2001 | Ross |
| 6,186,363 B1 | 2/2001 | Keller |
| 6,189,735 B1 | 2/2001 | Plasmati Lüchinger |
| 6,223,936 B1 | 5/2001 | Jeanbourquin |
| 6,231,615 B1 | 5/2001 | Preissman |
| 6,234,994 B1 | 5/2001 | Zinger |
| 6,238,182 B1 | 5/2001 | Mayer |
| 6,248,131 B1 | 6/2001 | Felt |
| 6,286,722 B1 | 9/2001 | Fischer |
| 6,290,101 B1 | 9/2001 | Chang |
| 6,325,249 B1 | 12/2001 | Keller |
| 6,332,894 B1 | 12/2001 | Stalcup |
| 6,345,776 B1 | 2/2002 | Hurray |
| 6,352,177 B1 | 3/2002 | Bublewitz |
| 6,382,466 B1 | 5/2002 | Schneider |
| 6,386,396 B1 | 5/2002 | Strecker |
| 6,394,314 B1 | 5/2002 | Sawhney |
| 6,395,032 B1 | 5/2002 | Gauchet |
| 6,395,034 B1 | 5/2002 | Suddaby |
| 6,402,784 B1 | 6/2002 | Wardlaw |
| 6,412,660 B1 | 7/2002 | Bouix |
| 6,419,702 B1 | 7/2002 | Ferree |
| 6,443,988 B2 | 9/2002 | Felt |
| 6,450,370 B2 | 9/2002 | Keller |
| 6,458,095 B1 | 10/2002 | Wirt |
| 6,482,234 B1 | 11/2002 | Weber |
| 6,499,630 B2 | 12/2002 | Mühlbauer |
| 6,540,113 B2 | 4/2003 | Gardos |
| 6,629,774 B1 | 10/2003 | Gruendeman |
| 6,691,932 B1 | 2/2004 | Schultz |
| 6,708,847 B2 | 3/2004 | Ljungquist |
| 6,719,729 B2 | 4/2004 | Sogaro |
| 6,719,797 B1 | 4/2004 | Ferree |
| 6,732,887 B2 | 5/2004 | Bills |
| 6,733,472 B1 | 5/2004 | Epstein |
| 6,752,292 B2 | 6/2004 | Van Herpen |
| 6,764,514 B1 | 7/2004 | Li |
| 6,769,574 B1 | 8/2004 | Keller |
| 6,812,211 B2 | 11/2004 | Slivka |
| 6,820,766 B2 | 11/2004 | Keller |
| 6,824,016 B2 | 11/2004 | Mühlbauer |
| 6,874,657 B2 | 4/2005 | Metzner |
| 6,874,661 B2 | 4/2005 | Timmerman |
| 6,923,813 B2 | 8/2005 | Phillips |
| 6,958,077 B2 * | 10/2005 | Suddaby .................. 623/17.11 |
| 6,969,404 B2 | 11/2005 | Ferree |
| 7,004,945 B2 | 2/2006 | Boyd |
| 2001/0004082 A1 | 6/2001 | Keller |
| 2001/0004710 A1 | 6/2001 | Felt |
| 2001/0013526 A1 | 8/2001 | Keller |
| 2002/0004594 A1 | 1/2002 | Borch |
| 2002/0010485 A1 | 1/2002 | Griego |
| 2002/0049498 A1 | 4/2002 | Yuksel |
| 2002/0138145 A1 | 9/2002 | Marchosky |
| 2002/0145007 A1 | 10/2002 | Sawhney |
| 2002/0156531 A1 | 10/2002 | Felt |
| 2002/0170926 A1 | 11/2002 | Horner |
| 2003/0082169 A1 | 5/2003 | Boyd |
| 2003/0137898 A1 | 7/2003 | Wagner |
| 2003/0195628 A1 | 10/2003 | Bao |
| 2003/0220649 A1 | 11/2003 | Bao |
| 2004/0045982 A1 | 3/2004 | Herman |
| 2004/0054414 A1 | 3/2004 | Trieu |
| 2004/0068268 A1 | 4/2004 | Boyd |
| 2004/0083002 A1 | 4/2004 | Belef |
| 2004/0104249 A1 | 6/2004 | Horth |
| 2004/0230309 A1 | 11/2004 | DiMauro |
| 2005/0055030 A1 | 3/2005 | Falahee |
| 2005/0069571 A1 | 3/2005 | Slivka |
| 2005/0119754 A1 | 6/2005 | Trieu |
| 2005/0130929 A1 | 6/2005 | Boyd |
| 2005/0131540 A1 * | 6/2005 | Trieu .................. 623/17.11 |
| 2005/0182418 A1 | 8/2005 | Boyd |
| 2005/0197707 A1 | 9/2005 | Trieu |
| 2005/0230422 A1 | 10/2005 | Muller |
| 2005/0245938 A1 | 11/2005 | Kochan |
| 2005/0251259 A1 | 11/2005 | Suddaby |
| 2006/0004457 A1 | 1/2006 | Collins |
| 2006/0004458 A1 | 1/2006 | Collins |

(56) References Cited

U.S. PATENT DOCUMENTS

| | | |
|---|---|---|
| 2006/0009778 A1 | 1/2006 | Collins |
| 2006/0009851 A1 | 1/2006 | Collins |
| 2006/0079905 A1 | 4/2006 | Beyar |
| 2006/0122704 A1 | 6/2006 | Vresilovic |
| 2006/0206118 A1 | 9/2006 | Kim |
| 2006/0247657 A1* | 11/2006 | Trieu ............................ 606/102 |
| 2006/0276802 A1 | 12/2006 | Vresilovic |
| 2007/0017931 A1 | 1/2007 | Sogaro |
| 2007/0023450 A1 | 2/2007 | Horth |
| 2007/0100349 A1 | 5/2007 | O'Neil |
| 2007/0179620 A1 | 8/2007 | Seaton |

FOREIGN PATENT DOCUMENTS

| | | |
|---|---|---|
| EP | 416471 | 1/1999 |
| EP | 937737 | 8/1999 |
| EP | 1223194 | 5/2004 |
| WO | WO 9531946 | 11/1995 |
| WO | WO 9902108 | 1/1999 |
| WO | WO 9942037 | 8/1999 |
| WO | WO 9953970 | 10/1999 |
| WO | WO 2005092249 | 10/2005 |

OTHER PUBLICATIONS

Alberts, R. et al., "Single Unit Artificial Intervertbral Disc", J. Neurosurg. Spine, 2004, vol. 1, pp. 95-100.

Ahrens, M. et al., "A New Procedure for Total Nucleus Removal From the Posterior Approach", European Cells and Materials, vol. 10(3). 2005, p. 3.

* cited by examiner

NUCLEUS AUGMENTATION DELIVERY DEVICE AND TECHNIQUE

REFERENCE TO RELATED APPLICATIONS

This application is a continuation of U.S. patent application Ser. No. 13/438,455 filed Apr. 3, 2012, (which granted as U.S. Pat. No. 8,357,199) which is a continuation of U.S. patent application Ser. No. 11/260,768, filed Oct. 27, 2005, (which granted as U.S. Pat. No. 8,197,545) both which are incorporated herein by reference.

BACKGROUND OF THE INVENTION

1. Field of the Invention

The present invention is directed to a device and method for determining the volume of intervertebral disc augmentation material needed to complete disc augmentation and the material's subsequent delivery. A second goal of this invention is to reduce leakage incurred when dispensing materials from a rigid cannula by improving the fit and fill of the annular wall defect.

2. Related Art

Some techniques for nucleus pulposus injection of materials like the SINUX® silicone disc augmentation material, utilize an injection cannula of rigid outer diameter to insert into the annular wall defect. Determination of the excised nucleus pulposus tissue is currently attempted via weight and/or volumetric measurement of the tissue following removal. Corresponding amounts of nucleus replacement material are injected into the disc space. Leakage of the injected material is a known issue when excess nucleus pulposus replacement material is added, correspondingly inadequate replacement of the nucleus can allow for device expulsion or improper functional spinal unit balance. Therefore accurate determination of the removed nucleus pulposus volume remains to be a challenge. Another issue present is the potential leakage of the injected material that may arise from an inadequate fit between the rigid injection cannula and the varying size annular wall defect(s).

Several nucleus pulposus and annular repair patents have been applied and issued. U.S. Patent Application Publication No. 2004/0068268 discloses cannulated distractors for maintaining disc height during replacement or augmentation of the spinal disc. U.S. Patent Application Publication No. 2003/0220649 describes interior liners and membranes such as balloons for in situ formation of nucleus replacement or augmentation materials. Bao et al. (European Cells and Materials, Vol. 10 Suppl. 3, 2005, p. 3), disclose assessing the shape and volume of the nucleus cavity in total nucleus removal procedures using an imaging balloon filled with contrast medium and fluoroscopic balloon images taken from multiple directions. However, none have been found that teach annular sealing for volumetric determination of the evacuated disc space and/or subsequent delivery of the disc replacement or augmentation material as hereinafter disclosed.

SUMMARY OF THE INVENTION

Figure 1A:
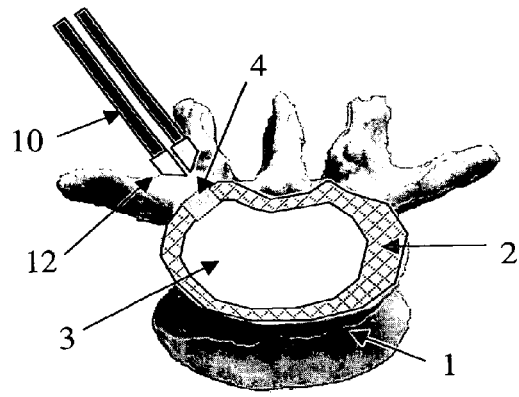
FIGS. 1a-1f depict one embodiment of this invention using a cannula with a conformable tip.

In accordance with one aspect of the present invention, a method of performing a procedure on an intervertebral disc comprises inserting a cannulated delivery tube through an opening in an annulus fibrosus of the intervertebral disc, positioning an expandable portion of the tube within the opening in the annulus fibrosus, expanding the expandable portion into contact with the annulus fibrosus about the opening to create a seal between the expandable portion and the annulus fibrosus, performing a procedure through the cannulated delivery tube within the annulus fibrosis, removing the tube, and closing the opening in the annulus fibrosus. The procedure performed may include injecting through the tube and the sealed opening in the annulus fibrosus an amount of a flowable nucleus pulposus replacement material directly into the annulus fibrosus. The expandable portion may comprise an expandable elastomeric gasket, in one embodiment, and the expandable portion may comprise an inflatable balloon, in another embodiment.

One advantage of this invention is its relatively easy determination of the volume of nucleus pulposus material removed as well as sealing of the annular wall defect to prevent intra-operative material leakage common when greater amounts than needed of nucleus pulposus material are injected to correct a disc defect.

DETAILED DESCRIPTION OF PREFERRED EMBODIMENTS OF THE INVENTION

Determination of the volume of nucleus pulposus material removed from the disc and prevention of leakage incurred during injection of nuclear replacement and/or augmentation materials are important aspects of intervertebral disc repair. Excessive injection and/or leakage of the replacement material(s) can initiate re-herniation or prompt herniation of the disc in another weakened annular location. Both of these failure modes can irritate neighboring tissues, including nerve roots, prompting additional pain and/or re-operation.

Insufficient nucleus pulposus injection can allow for continued disc height loss potentially leading to revision surgery.

The basic premise of this invention is that following a discectomy, a cannulated device is inserted into the surgically created annular wall defect. The annulus is sealed such that a known quantity of saline or other material can be injected and subsequently aspirated to determine volume of nucleus pulposus tissue removed. An equal volume of nucleus pulposus replacement material is injected or packed into the nucleus pulposus cavity through the device.

In making the volumetric determination of the defect to be repaired, a graduated syringe of known volume of volumetric material may be placed in to the cannulated device and injected into the intervertebral defect space, for example. Pressure can be applied to the material and monitored to insure full fill of small defects. A check valve with known pressure release can be utilized to ensure filling to a known pressure.

Suitable volumetric materials can be viscous and non-viscous including saline, gels, polymers, etc. Volumetric materials can be radio-opaque contrast agents, allowing fluoroscopic viewing during injection into the disc to a known pressure.

Examples of annular sealing techniques include: a conformable injection tip; an activated injection tip, and a balloon catheter injection tip. An optional embodiment of an internal valve to prevent backflow of either the saline or the nucleus pulposus replacement material is also disclosed. All sealing devices and methods maybe deployed extra-annularly, intra and/or inter-annularly (i.e., with respect to the annulus).

FIGS. 1a-1f, describe an injection cannula 10 with a conformable tip such as a soft elastomeric or foam gasket 12 around the injection tip of the cannula which is used to seal the annular defect. More specifically FIG. 1a depicts cannula 10 approaching surgically created hole or defect 4 in annulus fibrosus 2. The intervertebral disc space 3 formed by excision of nucleus pulposus is shown as empty. Adjacent vertebral body 1 shows the relative relationship affected disc to vertebral body 1. Gasket 12 can be comprised of varying shapes and geometries (ring, hourglass, tapered, etc.). Examples of suitable elastomeric or foam materials include but are not limited to thermoplastic elastomers, polypropylenes, polyethylenes, silicones, polyurethanes, latex, alloys and blends thereof.

Figure 1B:
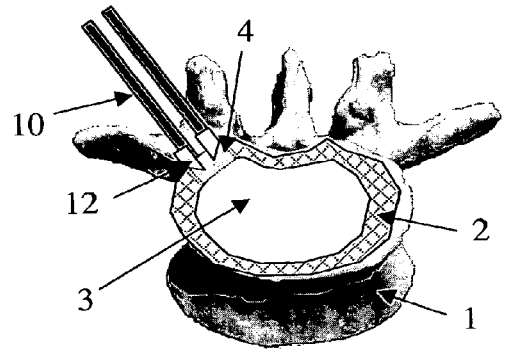
Figure 1C:
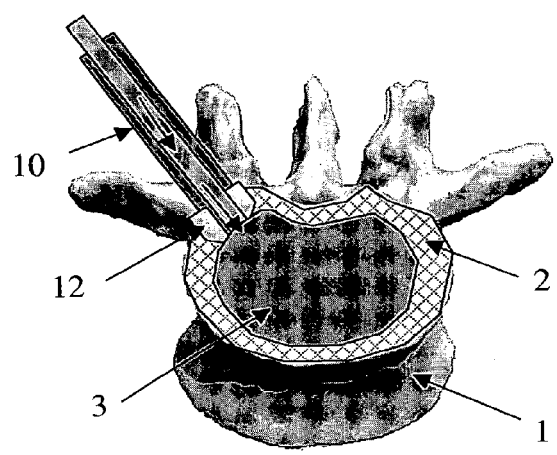
Figure 1D:
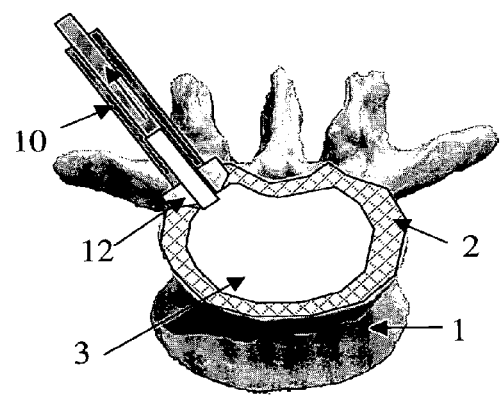
Figure 1E:
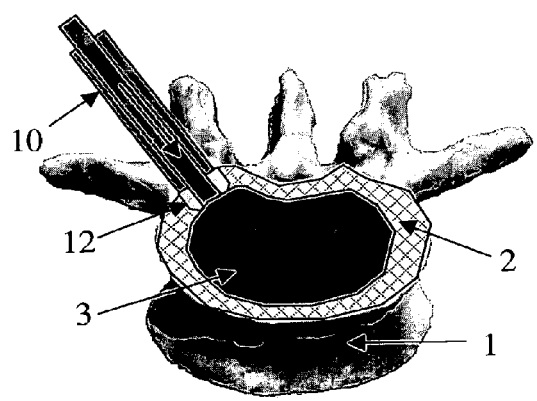
Figure 1F:
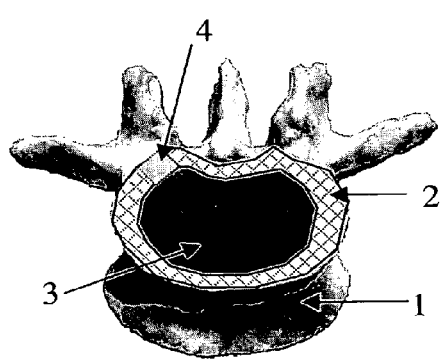

FIG. 1b shows cannula 10 being advanced into defect 4. FIG. 1c depicts the cannula 10 firmly engaged into defect 4 by virtue of gasket 12 so as to form an annular seal. FIG. 1d shows the volumetric material being introduced through cannula 10 into intervertebral disc space 3. The amount of volumetric material is measured or metered so as to determine the volume of cleared intervertebral disc space 3 that needs to be filled with a nucleus pulposus replacement or augmentation material. Once the volume of intervertebral disc space 3 is determined, intervertebral disc space 3 is evacuated in a preferred embodiment through cannula 10 as depicted in FIG. 1d. It should be noted that the volumetric material may be evacuated through another path, such as through another hole in the annulus fibrosus. FIG. 1e depicts the introduction of nucleus pulposus replacement or augmentation material through cannula 10 into intervertebral disc space 3. Once intervertebral disc space 3 is filled to the appropriate volume, cannula 10 is removed leaving annular hole or defect 4 open as shown in FIG. 1f. Defect 4 may be closed by any suitable closure techniques known in the art such as through use of an annular plug or by surgical suturing.

Figure 2A:
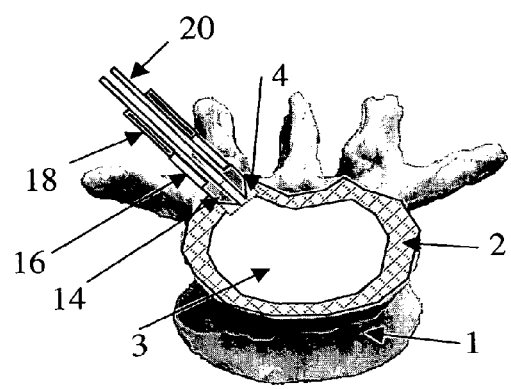
FIGS. 2a-2b depict another embodiment of this invention using a cannula with an expandable tip.
Figure 2B:
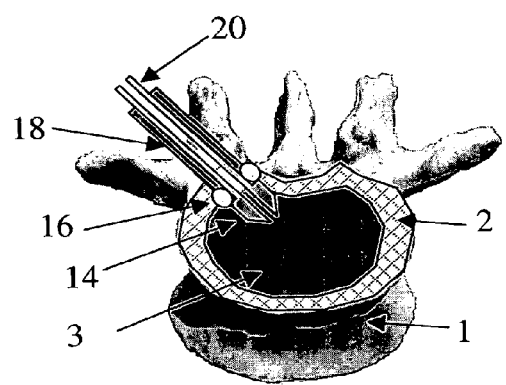

FIGS. 2a-2b describe one embodiment of a device of this invention wherein a volumetric material delivery device comprises an expandable elastomeric tip or foam gasket. More particularly, FIG. 2a depicts the device comprising inner cannula 20 and outer cannula 18. Disposed between cannula 18 and 20 is elastomeric gasket 16. FIG. 2b shows the device in activation wherein the relative position of internal cannula 20 has changed with respect to outer cannula 18 so as to cause gasket 16 to bulge or radially expand and thereby form a firm seal of annular defect 4 and allow for substantially leak proof delivery of the volumetric material. The bulging of gasket 16 may be caused, for example, by pushing external cannula 18 to create the desired seal, or conversely by pulling of e internal cannula 20 to expand for the desired amount of seal. Multiple shapes and materials for gasket 16 may be utilized as described above for gasket 12.

Figure 3A:
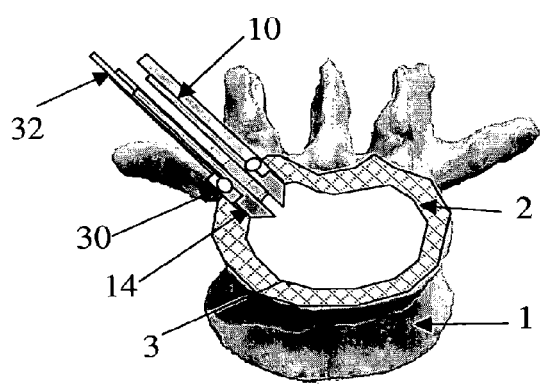
FIGS. 3a-3b depict yet another embodiment of this invention using a cannula with an inflatable balloon tip.
Figure 3B:
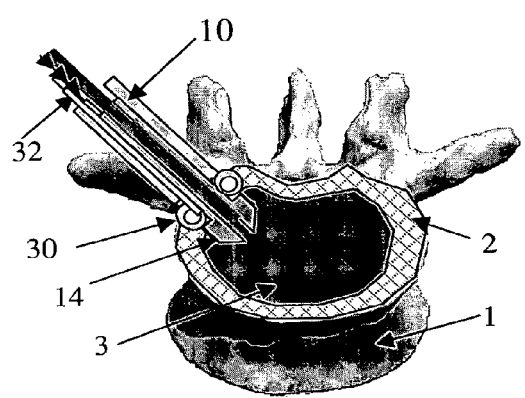

FIGS. 3a and 3b describe yet another device for forming a seal via a ballooning tip. Specifically, FIG. 3a describes a cross-sectional view of cannula 10 comprising catheter tube 32 and inflatable balloon 30. Tube 32 acts a passageway to provide air or gas to the annular balloon 30 for inflation. FIG. 3b shows the device in operation wherein balloon 30 has been inflated to firmly seal annulus fibrosus prior to volumetric material being introduced into intervertebral disc space 3. Balloon 30 may be produced from any thin biocompatible flexible polymer known in the art.

Figure 4A:
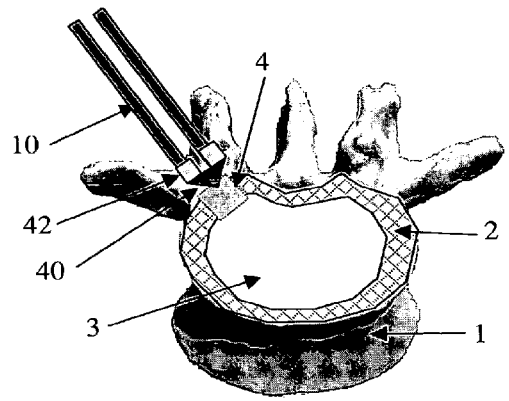
FIGS. 4a-4f depict another embodiment of this invention using a cannula with an anti backflow check valve.

FIGS. 4a-4f depict a preferred embodiment of this invention which utilizes an internal check valve to preclude backflow of either volumetric material and/or the nucleus pulposus replacement material. Referring to FIG. 4a, cannula 10 comprises anti-backflow valve 40 and annular sealing means 42. It should be noted that annular sealing means 42 may be any of the above described sealing techniques, e.g., conformable tip, expanding gasket or inflating balloon. Valve 40 may be activated to allow for aspiration and/or removal of the volumetric material or excess nucleus pulposus replacement or augmentation material.

Figure 4B:
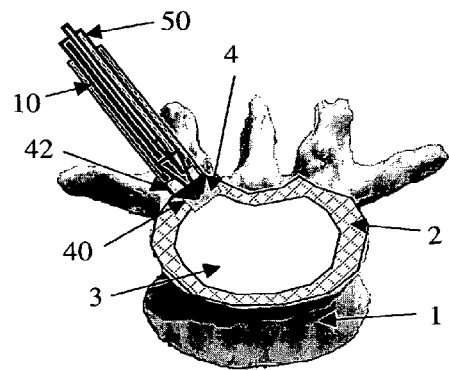
Figure 4C:
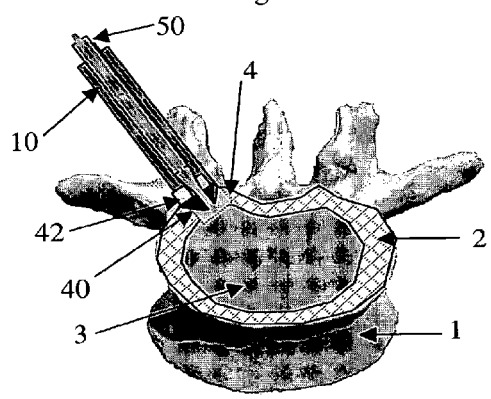
Figure 4D:
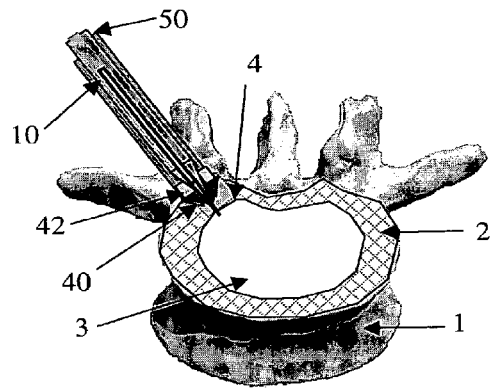
Figure 4E:
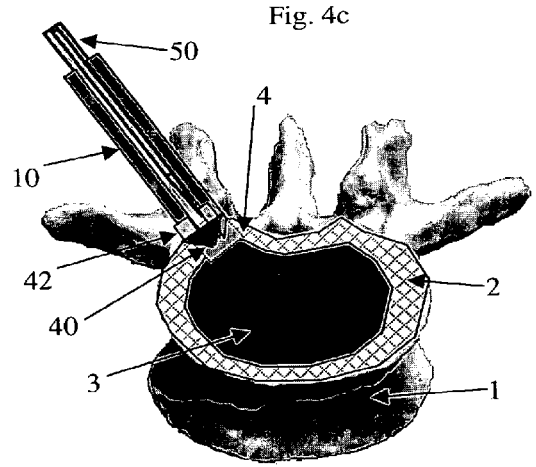
Figure 4F:
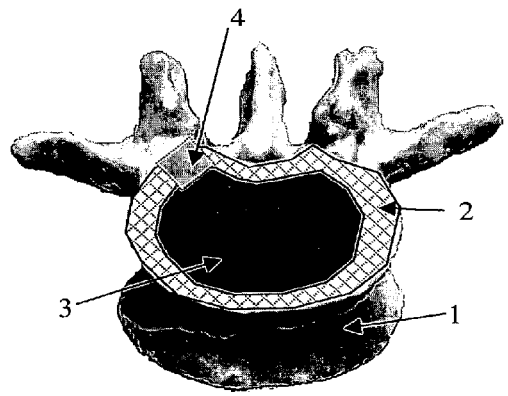

A further preferred embodiment as shown in FIG. 4b, a cannulated stylet 50 is inserted into the cannula 10 which has been sealed into annular defect 4. In dispensing volumetric material into intervertebral disc space 3, stylet 50 is advanced, as depicted in FIG. 4c to permit entry into intervertebral space 3. Once the amount of volumetric material has been determined, stylet 50 is used in reverse fashion to withdraw the volumetric materials such as through aspiration, as shown in FIG. 4d. Once intervertebral space 3 has been evacuated of the volumetric material, the nucleus replacement or augmentation material is injected into intervertebral disc space 3 as shown in FIG. 4e. Finally, FIG. 4f shows intervertebral disc space 3 filled with the appropriate volume of nucleus replacement or augmentation material with cannula 10 having been removed leaving annular hole or defect 4. Defect 4 may be closed by any suitable closure techniques known in the art such as through use of an annular plug or by surgical suturing. While this one technique for valve activation has been shown by insertion of the tip of an injector or stylet into the valve to facilitate opening, any other known techniques common to valve technology may be employed in activating anti-back flow valve 40.

Suitable materials for use as the nucleus pulposus replacement or augmentation material may be of any known type. Examples of such materials include, but are not limited to polyethylenes, silicones, polyurethanes, metallics, ceramics, collagen, hydrogels, for example.

It should be understood that the foregoing disclosure and description of the present invention are illustrative and explanatory thereof and various changes in the size, shape and materials as well as in the description of the preferred embodiment may be made without departing from the spirit of the invention. For example, it is envisioned that this invention may be applied to correcting defects in other articulating joints were volumetric determination of a defect is a benefit, such as with knees, hips, shoulders, elbow capsules as best examples, but also to facets, ankles, wrists, hand, and digits.

What is claimed is:

1. A method of delivering a nucleus pulposus replacement material comprising:
    removing nucleus pulposus material from an intervertebral disc;
    inserting a cannulated delivery tube through an opening in an annulus fibrosus of the intervertebral disc, the cannulated delivery tube including an inflatable annular balloon disposed proximate a distal portion of the delivery tube;
    inflating the inflatable annular balloon of the cannulated delivery tube against the annulus fibrosus about the opening to create an annular seal between the inflatable annular balloon of the cannulated delivery tube and the annulus fibrosus and thereby seal the opening in the annulus fibrosus;
    injecting a known amount of volumetric material through the cannulated delivery tube and the sealed opening directly into the annulus fibrosus, and not into an implant placed in the annulus fibrosus, to determine the volume of nucleus pulposus material removed from the intervertebral disc, removing the volumetric material injected in the annulus fibrosus;

delivering through the cannulated delivery tube and the sealed opening in the annulus fibrosus an amount of a nucleus pulposus replacement material directly into the annulus fibrosus and not into an implant placed in the annulus fibrosus, the amount of nucleus pulposus replacement material being based on the amount of volumetric material injected;

removing the cannulated delivery tube; and closing the opening in the annulus fibrosus.

2. The method of claim 1, wherein the inflatable annular balloon is positioned extra-annularly.

3. The method of claim 1, wherein the inflatable annular balloon is positioned intra-annularly.

4. The method of claim 1, wherein the inflatable annular balloon is positioned inter-annularly.

5. The method of claim 1, wherein the nucleus pulposus replacement material comprises at least one of polyethylenes, silicones, polyurethanes, metallics, ceramics, collagen, and hydrogels.

6. The method of claim 1, wherein the nucleus pulposus replacement material is injected into the annulus fibrosus through the cannulated delivery tube.

7. The method of claim 1, wherein the nucleus pulposus replacement material is packed into the annulus fibrosus through the cannulated delivery tube.

8. The method of claim 1, wherein the volumetric material comprises at least one of saline, gels, or polymers.

9. The method of claim 1, wherein the volumetric material includes a radio-opaque contrast agent.

10. The method of claim 1, wherein the cannulated delivery tube further comprises a check valve to prevent backflow of the volumetric material or the nucleus pulposus replacement material.

11. A method of delivering a nucleus pulposus replacement material comprising:

removing nucleus pulposus material from an intervertebral disc;

inserting a cannulated delivery tube through an opening in an annulus fibrosus of the intervertebral disc, the cannulated delivery tube including a gasket disposed proximate a distal portion of the delivery tube;

creating an annular seal between the gasket of the cannulated delivery tube and the annulus fibrosus and thereby seal the opening in the annulus fibrosus;

injecting a known amount of volumetric material through the cannulated delivery tube and the sealed opening directly into the annulus fibrosus, and not into an implant placed in the annulus fibrosus, to determine the volume of nucleus pulposus material removed from the intervertebral disc;

removing the volumetric material injected in the annulus fibrosus;

delivering through the cannulated delivery tube and the sealed opening in the annulus fibrosus an amount of a nucleus pulposus replacement material directly into the annulus fibrosus and not into an implant placed in the annulus fibrosus, the amount of nucleus pulposus replacement material being based on the amount of volumetric material injected;

removing the cannulated delivery tube; and closing the opening in the annulus fibrosus.

12. The method of claim 11, wherein the gasket is an expandable gasket.

13. The method of claim 11, wherein the gasket is one of a soft elastomeric gasket and a foam gasket.

14. The method of claim 11, wherein the gasket is shaped as one of a ring, an hourglass, and tapered.

15. The method of claim 11, wherein the nucleus pulposus replacement material comprises at least one of polyethylenes, silicones, polyurethanes, metallics, ceramics, collagen, and hydrogels.

16. The method of claim 11, wherein the nucleus pulposus replacement material is packed into the annulus fibrosus through the cannulated delivery tube.

17. The method of claim 11, wherein the volumetric material comprises at least one of saline, gels, or polymers.

18. The method of claim 11, wherein the volumetric material includes a radio-opaque contrast agent.

19. The method of claim 11, wherein the cannulated delivery tube further comprises a check valve to prevent backflow of the volumetric material or the nucleus pulposus replacement material.

* * * * *